(12) United States Patent
Lalla et al.

(10) Patent No.: US 10,338,072 B2
(45) Date of Patent: Jul. 2, 2019

(54) METHOD OF DETECTING CANCER

(71) Applicant: Sienna Cancer Diagnostics Ltd, Scoresby, Victoria (AU)

(72) Inventors: Minesh Lalla, Moonee Ponds (AU); Fabio Turatti, Docklands (AU); Sharyn Wilson, Mont Albert (AU)

(73) Assignee: Sienna Cancer Diagnostics Ltd, Scoresby (AU)

( * ) Notice: Subject to any disclaimer, the term of this patent is extended or adjusted under 35 U.S.C. 154(b) by 0 days.

(21) Appl. No.: 15/116,182

(22) PCT Filed: Feb. 17, 2015

(86) PCT No.: PCT/AU2015/050060
§ 371 (c)(1),
(2) Date: Aug. 2, 2016

(87) PCT Pub. No.: WO2015/120523
PCT Pub. Date: Aug. 20, 2015

(65) Prior Publication Data
US 2017/0176438 A1 Jun. 22, 2017

(30) Foreign Application Priority Data
Feb. 17, 2014 (AU) .................. 2014900494

(51) Int. Cl.
*G01N 33/573* (2006.01)
*G01N 33/574* (2006.01)

(52) U.S. Cl.
CPC ..... *G01N 33/57407* (2013.01); *G01N 33/574* (2013.01); *G01N 2333/9128* (2013.01)

(58) Field of Classification Search
None
See application file for complete search history.

(56) References Cited

U.S. PATENT DOCUMENTS

2009/0142259 A1* 6/2009 Gao .................. G01N 33/57407
514/1.1

FOREIGN PATENT DOCUMENTS

| WO | 2002/073204 | 9/2002 |
| WO | WO2006089287 | 8/2006 |
| WO | 2009/075803 | 6/2009 |

OTHER PUBLICATIONS

Yan, P., et al., Histochem Cell Biol 121:291-397, 2004.*
Hashimoto, Y., et al., Surgery, 143: 113-125, 2008.*
Sanchini et al (Neoplasia 6:234-239, 2004 (Year: 2004).*
Anti-telomerase antibodies (rabbit, Millipore Sigma , available online Jan. 2004 (Year: 2004).*
Xie et al (Ann Clin Biochem (44:523-528, 2007 (Year: 2007).*
Khalbuss, W. et al., 'Immunohistochemical detection of hTERT in urothelial lesions: a potential adjunct to urine cytology', CytoJournal, 2006, 3(18):1-8.
Osawa, N. et al., 'Diagnosis of parathyroid carcinoma using immunohistochemical staining against hTERT', International Journal of Molecular Medicine, 2009, 24:733-741.
Zhao, P. et al., 'Expressions of telomerase reverse transcriptase and fragile histidine triad in human ovarian carcinoma', Chinese Journal of Cancer Prevention and Treatment (Zhongliu Fangzhi Zazhi), 2004, 11:1278-1281.
Duarte, M.G. et al., 'Expression of TERT in precancerous gastric lesions compared to gastric cancer', Brazilian Journal of Medical and Biological Research, 2011, 44:100-104.
Luzar, B. et al., 'Telomerase catalytic subunit in laryngeal carcinogenesis—an immunohistochemical study', Modern Pathology, 2005, 18:406-411.
Hiyama, E. et al., 'Immunohistochemical detection of telomerase (hTERT) protein in human cancer tissues and a subset of cells in normal tissues', Neoplasia, 2001, 3:17-26.
Communication, The Extended European Search Report for PCTAU2015050060, dated Aug. 31, 2017, 10 pages.
Simon, et al. "Tubal metaplasia of the endometrium with cytologic atypia: analysis of p53, Ki-67, TERT, and long-term follow-up", Mod Pathol. Sep. 2011;24(9):1254-61.
Wu, Ying-Li, et al., (2006) "Immunodetection of human telomerase reversetranscriptase (hTERT) re-appraised: nucleolin and telomerase cross paths", Journal of Cell Science, 119(13):2797-2806.

* cited by examiner

*Primary Examiner* — Lei Yao
(74) *Attorney, Agent, or Firm* — Carol L. Francis; Bozicevic, Field & Francis LLP

(57) ABSTRACT

The disclosure provides methods for resolving an inconclusive cytological assessment of clinically relevant cells in a sample obtained from a patient based on the cytological detection of antibody binding to telomerase in clinically relevant cells in the sample, wherein binding of the antibody to clinically relevant cells indicates the presence of malignant or cancerous cells.

8 Claims, 3 Drawing Sheets

METHOD OF DETECTING CANCER

TECHNICAL FIELD

Figure 1:
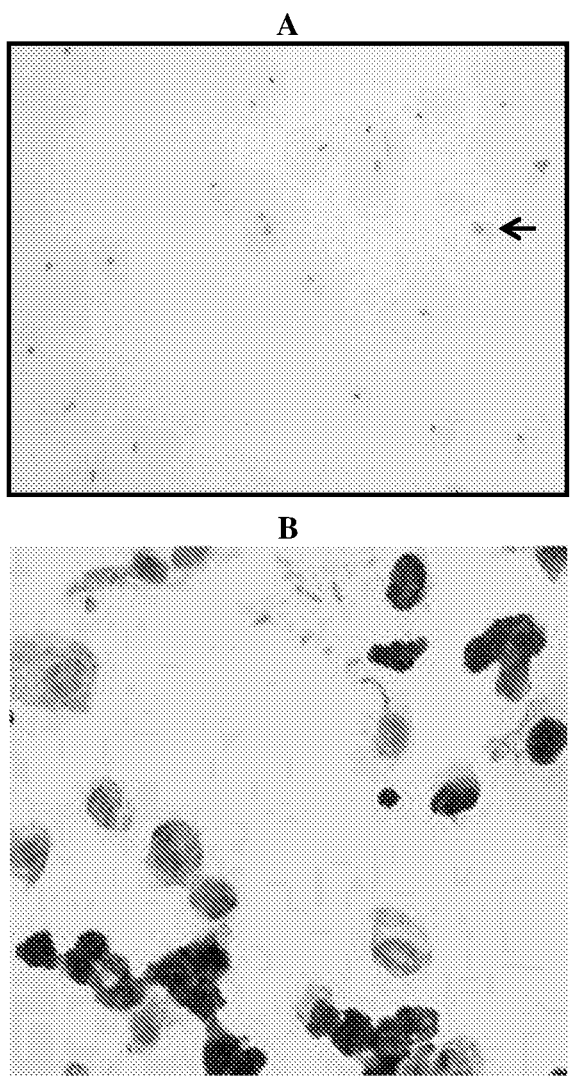

The present disclosure relates to methods of determining whether a subject has cancer. More particularly, the present disclosure relates to a method of determining whether a subject has cancer when a cytological assessment of cell morphology is inconclusive for the cancer.

BACKGROUND OF THE INVENTION

The development and progression of cancer places a significant emotional and financial burden on society.

Bladder cancer is the second most common genitourinary tumour in human populations, with an incidence of approximately 261,000 new cases each year worldwide; about a third of those are likely to be invasive or metastatic disease at the time of diagnosis (Parkin et al., 1999).

As with many other cancers, clinical diagnosis of bladder cancer can be a difficult process, particularly in the early stages of cancer development. At present, cystoscopy and urine cytology are the most important tools in the diagnosis and follow-up of bladder cancer.

At present, cystoscopy with biopsy is generally considered the gold standard for diagnosing bladder cancer. A drawback to using cystoscopy is that it requires an invasive procedure. In addition to being invasive, obtaining a biopsy via cystoscopy can have potential adverse outcomes for the patient. Given these limitations, it is very difficult to obtain patient samples via cystoscopy, repeatedly from a large number of individuals.

Accordingly, clinicians generally rely on routine cytology to identify patients at risk of developing bladder cancer prior to cystoscopy. Routine cytology suffers from two well accepted limitations that reduce its utility as a diagnostic tool for early stage cancer.

First, cytology has poor sensitivity for low grade cancer. Accordingly, routine cytology returns a high level of false-negative results in low-grade cancer samples that completely lack cellular morphological abnormalities. Second, the usefulness of cytology for the detection of low grade disease, or hard to diagnose lesions, is limited. For example, when using cytology for the diagnosis of bladder cancer, a large proportion of cases (20-25%) are reported as atypical, including "atypical urothelial cells of unknown significance" (AUCUS) and "atypical urothelial cells, cannot exclude high-grade urothelial carcinoma (AUHGC)" (Rosenthal et al., 2013). A reported outcome of AUCUS or AUHGC is of little or no diagnostic utility.

A need therefore exists for a method capable of providing a more accurate, early and economically viable diagnosis of cancers. Such a method could provide assistance to clinicians in reaching an early stage diagnosis prior to the portrayal of detectable morphological indicators. Moreover, early diagnosis of cancer, prior to invasion and metastasis, is generally associated with improved prognosis. Accordingly, there is a social and economic imperative to provide a method that can more reliably detect cancer at an early stage, so anti-cancer therapy can be administered at a time when the disease burden is mild.

SUMMARY OF THE INVENTION

The present disclosure can be used to assist in resolving an inconclusive cytological assessment of cancer, and hence may be used as a reflexive test to inconclusive cytological assessment procedures. Thus, in a first aspect, the present disclosure provides a method of resolving an inconclusive cytological assessment of clinically relevant cells in a sample obtained from a patient, the method comprising contacting cells from the sample with an anti-telomerase antibody and performing a cytological assessment of the cells to detect binding of the antibody to clinically relevant cells, wherein binding of the antibody to clinically relevant cells indicates the presence of malignant cells.

The method of the present disclosure may be used to resolve an inconclusive cytological assessment of clinically relevant cells in a sample obtained from a patient.

For example, the methods of the present disclosure may comprise contacting a patient sample comprising clinically relevant cells of inconclusive cytology with an anti-telomerase antibody and detecting the presence or absence of binding of the antibody to the clinically relevant cells of inconclusive cytology, wherein binding of the antibody to clinically relevant cells of inconclusive cytology indicates the presence of malignant cells.

In an embodiment of the above aspect, the absence of antibody binding to clinically relevant cells indicates that malignant cells are not present in the sample.

In a further aspect, the present disclosure relates to a method of determining whether a subject has cancer when a cytological assessment of cell morphology is inconclusive for the cancer, the method comprising:

i) contacting a cell sample from the subject with an anti-telomerase antibody;

ii) performing a cytological assessment of the cell sample to detect binding of the antibody to clinically relevant cells in the sample;

wherein binding of the antibody to one or more clinically relevant cells in the sample indicates that the subject has cancer.

When cancer is determined using a method of the disclosure the determination may or may not be conclusive with respect to the definitive diagnosis upon which a treating physician will determine a course of treatment. The definitive diagnosis of the cancer status of a subject determined to have cancer can be validated or confirmed if warranted, such as through imaging techniques including, PET, MRI, ultrasound, CT, PET/CT. In an embodiment of the above aspects, when the cancer being determined is bladder cancer, further investigation via cystoscopy with biopsy or upper tract imaging may be used to obtain a definitive diagnosis of the cancer status.

The present disclosure can also be used as a frontline, adjunctive test, to more accurately determine the presence of malignant cells in a single procedure. Accordingly, in a further aspect, the present disclosure provides a method of determining whether a subject has cancer, the method comprising:

i) performing a cytological assessment of cell morphology on a cell sample from the subject to determine the morphology of one or more clinically relevant cells in the sample;

ii) contacting a cell sample from the subject with an anti-telomerase antibody and performing a cytological assessment of the cell sample to detect binding of the antibody to clinically relevant cells in the sample;

wherein when the cytological assessment of cell morphology is inconclusive for the cancer, binding of the antibody to one or more clinically relevant cells indicates that the subject has cancer.

In an embodiment of the above aspects, binding of the antibody to at least about 5% of clinically relevant cells in the sample indicates that the subject has cancer.

Further, the cytological morphological assessment and detection of telomerase can be performed in any order or simultaneously on the same cells.

In an embodiment, binding of an anti-telomerase antibody to cells with an atypical cytology indicates that the subject has cancer. For example, the methods of the present disclosure identifies the subject as having a malignant cancer when binding of the antibody to cells with an atypical or indeterminate cytology is detected.

In an embodiment, the absence of anti-telomerase antibody binding to clinically relevant cells indicates that the cells in the sample are not malignant. For example, the methods of the present disclosure identifies the subject does not have malignant cancer cells when antibody binding to clinically relevant cells is not detected.

In another embodiment, the methods of the present disclosure comprises directing treatment of the subject for a malignant cancer when binding of the antibody to cells with an atypical or indeterminate cytology is detected.

As will be appreciated by one of skill in the art, cytological assessment involves the assessment of individual cells. Accordingly, in performing the present method the individual cells are cytologically assessed to detect binding of an anti-telomerase antibody to clinically relevant cells. Cytological assessment of telomerase allows telomerase stained cell types which are known to be non-cancerous to be excluded from the assessment based on their morphology. For example, the methods of the present disclosure comprise excluding non-clinically relevant cells from the cytological assessment.

Excluded cells are considered not clinically relevant to determining whether a subject has cancer. The excluded cells will depend on the cancer being detected. More specifically, the skilled person will be aware of cell types in a sample related to a particular cancer. Examples of excluded cells include, but are not necessarily limited to, one or more or all of T-cells, B-cells, neutrophils, macrophages, granulocytes, dendritic cells, mast cells, memory-cells, plasma cells, eosinophils, renal tubular cells, seminal vesicle cells, sperm, and squamous cells. For example, the cells listed above will be excluded when assessing bladder cancer using the methods of the disclosure.

The sample can be any suitable type known to potentially include malignant cells. Examples of suitable samples include, but are not necessarily limited to, biopsy material, resection material, urine, bladder washings, bladder scrubbings, blood, sputum, cerebrospinal fluid, pleural effusions, abdominal ascites, liver, thyroid, ovary, lymph node, breast, cervix, lung, biliary tree, pancreas, lung and colon. In an embodiment, the sample is a fluid sample.

In an embodiment, the cancer is bladder cancer and the sample is urine, bladder washings or bladder scrubbings.

The antibody may have a variety of different forms such as, but not limited to, monoclonal, polyclonal, bispecific, chimeric, recombinant, anti-idiotypic, humanized, single-chain antibody molecule, or antigen-binding fragments thereof.

Examples of antibodies suitable for use in the disclosure include, but are not limited to, SCD-A7, 2D8, C-12, H-231, anti-telomerase catalytic subunit, 10E9-2, 2C4, and tel 3 36-10. In an embodiment, the antibody is SCD-A7 or a telomerase binding fragment thereof.

The cancer can be any cancer where clinically relevant cells may be present which can result in an inconclusive cytological assessment for the cancer. For example, the cancer can be an epithelial cancer. Other examples of cancers include, but are not necessarily limited to, bladder cancer, pancreatic cancer, liver cancer, gall bladder cancer, thyroid cancer, breast cancer, lung cancer, mesothelioma, cervical cancer, ovarian cancer, kidney cancer, lymphoma and colorectal cancer. In an embodiment the cancer is bladder cancer.

In a further aspect the present disclosure provides a method of resolving an inconclusive cytological assessment of bladder epithelial cells in a urine sample obtained from a patient, the method comprising contacting epithelial cells from the sample with an anti-telomerase antibody and performing a cytological assessment of the epithelial cells to detect binding of the antibody to the epithelial cells, wherein binding of the antibody to the epithelial cells indicates the presence of malignant cells.

In a further aspect the present disclosure provides a method of determining whether a subject has bladder cancer when a cytological assessment of bladder epithelial cell morphology that is inconclusive for bladder cancer, the method comprising:

i) contacting a sample of bladder epithelial cells from the subject with an anti-telomerase antibody;

ii) performing a cytological assessment of the bladder epithelial cells to detect binding of the antibody to the bladder epithelial cells;

wherein binding of the antibody to one or more bladder epithelial cells in the sample indicates that the subject has cancer.

In a further aspect the present disclosure provides a method of determining whether a subject has bladder cancer, the method comprising:

i) performing a cytological assessment of cell morphology on a sample of bladder epithelial cells from the subject to determine the morphology of one or more bladder epithelial cells in the sample;

ii) contacting a sample of bladder epithelial cells from the subject with an anti-telomerase antibody and performing a cytological assessment of the bladder epithelial cells to detect binding of the antibody to the bladder epithelial cells;

wherein when the cytological assessment of cell morphology is inconclusive for bladder cancer, binding of the antibody to one or more bladder epithelial cells indicates that the subject has cancer.

In a further aspect, the present disclosure provides a method of resolving an inconclusive cytological assessment of bladder epithelial cells in a urine sample obtained from a patient, the method comprising contacting a patient sample comprising bladder epithelial cells of inconclusive cytology with an anti-telomerase antibody and detecting the presence or absence of binding of the antibody to the bladder epithelial cells of inconclusive cytology, wherein binding of the antibody to bladder epithelial cells of inconclusive cytology indicates the presence of malignant cells.

In an embodiment the bladder epithelial cells are bladder urothelial cells.

The present disclosure is not to be limited in scope by the specific embodiments described herein, which are intended for the purpose of exemplification only. Functionally-equivalent products, compositions and methods are clearly within the scope of the disclosure, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The disclosure is hereinafter described by way of the following non-limiting Examples and with reference to the accompanying figures.

BRIEF DESCRIPTION OF THE ACCOMPANYING DRAWINGS

FIG. 1: No cellular staining was observed in sample WH11-107 (clinically negative; FIG. 1A). First evidence of immunostaining of telomerase and its clinical correlation shown in clinically positive sample WH11-122 using the anti-hTERT (Clone 2C4) antibody (FIG. 1B). Positive nuclear staining was observed in 40-75% of the urothelial cells present, under optimal antibody concentrations.

Figure 2:
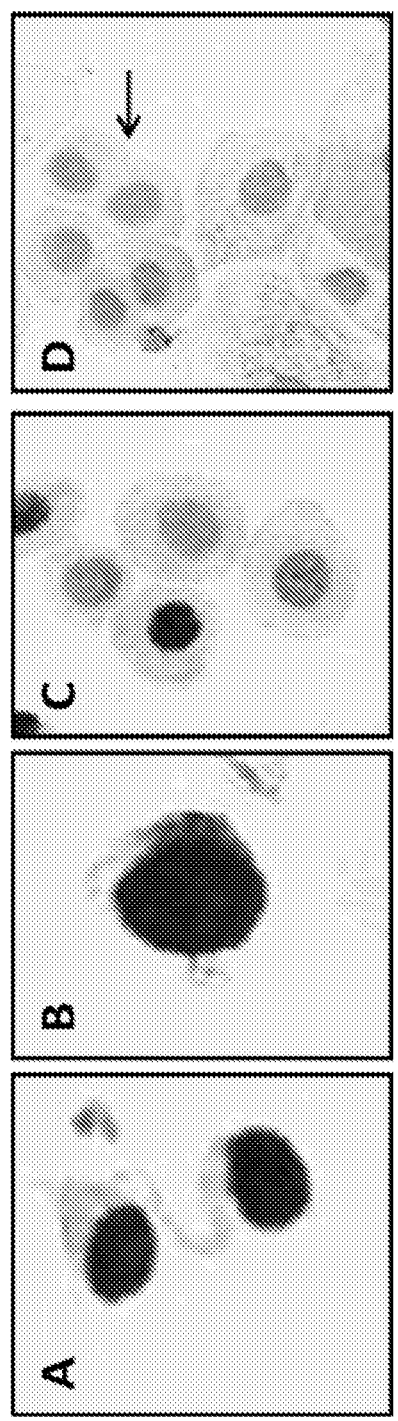

FIG. 2: Positive and negative cell types observed in high grade (Panel A and B) and low grade (Panel C and D) clinical samples. Atypical urothelial cells stained nuclear positive by telomerase immunostaining (Panel A and B). Cytologically normal looking urothelial cells stained nuclear positive by telomerase immunostaining (Panel C) and within the same sample unstained cytologically normal looking urothelial cells (Panel D, inset arrow).

Figure 3:
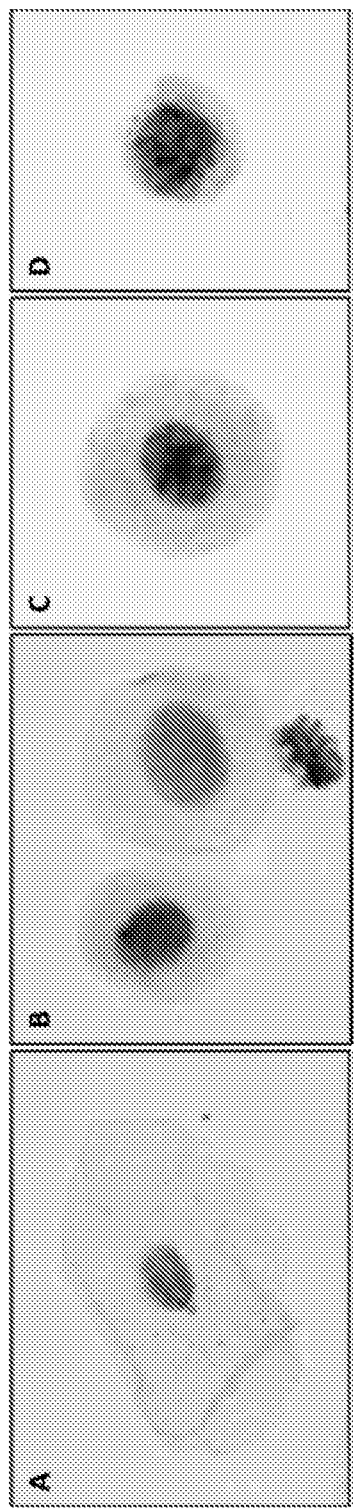

FIG. 3: Cells stained for telomerase hTERT protein from a clinical sample of a patient with low grade (G1) bladder cancer. Panel A: Squamous cell (not from bladder); Panel B: Normal bladder cells (and small brown blood cell); Panel C: Normal-looking bladder cell positive for Sienna test; Panel D: Cytologically abnormal bladder cell positive for telomerase immunostaining.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, cancer diagnostics, immunology, immunohistochemistry, protein chemistry, and biochemistry).

Unless otherwise indicated, the immunoassay, sample preparation, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10%, more preferably +/−5%, more preferably +/−1%, more preferably +/−0.5% of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Cytological Assessment

"Cytological assessment" of cell morphology in cancer diagnostics seeks to identify malignant cells based on morphologic characteristics. Cytological assessment of cell morphology is a procedure that is part of the standard of care and used alongside, or as a reflex to, further investigation for the detection of recurrence or the diagnosis of cancer. It is not a test per se but a pathology consultation based on a particular sample or sample set. The assessment procedure is complex and requires expertise and care in sample collection to provide a correct assessment. In the context of bladder cancer, cytological assessment can be used alongside, or as a reflex to, cystoscopy for the detection of recurrence or the diagnosis of bladder cancer.

In performing a cytological assessment of cell morphology, a cell sample is typically fixed to a slide and viewed under a microscope to visually assess the morphology and cellular features. For example, bladder urothelial cells can be harvested from a urine sample, fixed to a slide and then visually assessed.

Before, visually assessing the slide, the sample may be stained to assist in visualising morphological changes to cells and cellular components (e.g. nuclei). These stains can include a haematoxylin and eosin stain or Papanicolaou stain (Pap stain).

Historically, the performance of cytology was described as extremely good with high-grade cancer but more recent studies have challenged that perception. On the other hand, the majority of studies to date are in general agreement regarding the low sensitivity of cytology in low grade cancer. Accordingly, cytological assessment can often be inconclusive and not achieve its intended goal to aid in the diagnosis of cancer. Further, given the low sensitivity of cytological assessment, a negative or inconclusive cytology result does not preclude the presence of cancer (especially low grade cancer).

Inconclusive Cytological Assessment of Cell Morphology

As used herein, an "inconclusive cytological assessment of cell morphology" is inconclusive for cancer and therefore is not informative for reaching a cancer diagnosis. More particularly, an "inconclusive cytological assessment of cell morphology" refers to an assessment that identifies cells that have lost their normal appearance but have not reached the level of abnormality of malignant cells.

Cells that have lost their normal appearance but have not reached the level of abnormality of malignant cells are commonly referred to in the art as cells with atypical or indeterminate cytology. Therefore, in the context of the present methods, an "inconclusive cytological assessment of cell morphology" is one which reveals that one or more clinically relevant cells in a sample obtained from the subject have atypical or indeterminate cytology.

Terms "atypical cytology" or "indeterminate cytology" can be used interchangeably to indicate an inconclusive cytological assessment. In the context of the present disclosure, cells with "atypical cytology" have lost their normal appearance but have not reached the level of abnormality of malignant cells.

One of skill in the art would be aware of various morphological cues that indicate such cytology. An atypical call in cytology is determined by one skilled in the art and indicates that they believe the morphological cues are sufficiently poorly defined so as to allow a definitive call as either positive or negative by cytology. The call in these cases will vary depending on the lab or the specialist, and may include for example, "atypical" or "atypical cytology", "atypia", "indeterminate" or "indeterminate cytology", "inconclusive" or "inconclusive cytology", "equivocal" or "unknown". Such calls are inconclusive cytological assessments.

Examples of atypical cytology features are provided below. "Atypical" or "atypia" are pathologic terms for a morphological abnormality in a cell. Morphological changes, at a cellular level, that may be associated with atypia and therefore, "atypical cytology" can include, densely stained nuclei, pleomorphic nuclei, altered nucleus: cytoplasm ratio, aberrant mitosis, frequent mitosis, suprabasal mitosis, de-differentiation, loss of cellular adhesion, loss of cellular polarity, apoptosis.

In cytological assessments for cancer, such as thyroid carcinoma, breast cancer or bladder cancer an inconclusive cytological assessment can be reported as "atypical cytology".

For example, thyroid samples with a moderate amount of colloid and moderate cellularity and/or, follicular cells present in groups showing significant crowding and overlapping can be difficult to classify as either benign or malignant and therefore are often reported as "indeterminate".

For many cancers, the cellular features associated "atypical cytology" can be dependent on the cytologist and their clinical practice. This can result in, "atypical cytology" being divided into various classifications.

For example, various classifications associated with "atypical cytology" in thyroid carcinoma are exemplified in Table 1.

In bladder cancer, "atypical cytology" may be separated into low-grade atypia or high-grade atypia. Histological features associated with low-grade atypia in bladder cancer include, papilloma, papillary hyperplasia and papillary urothelial neoplasm of low malignant potential. Histological features associated with high-grade atypia in bladder cancer include atypia that falls short of carcinoma in situ but with marked focal cytologic atypia and disorganised architecture. Histological features defined as atypical, that are also indicative of High Grade Urothelial Carcinoma can include individual abnormal cells, hyperchromatic nuclei, irregular nuclear borders, increased nuclear:cytoplasm ratio, anisonucleosis, elongated nuclei and cell clusters.

TABLE 1

Exemplary features associated with "atypical cytology" for thyroid carcinoma.

| Cytology classification | Features |
|---|---|
| Atypical cells present | Mostly benign cells but including a few that are atypical in appearance where malignancy is an unlikely possibility. |
| Atypia of undetermined significance | Prominent population of micro follicles in an aspirate that does not otherwise fulfil the criteria for "follicular neoplasm/suspicious for follicular neoplasm. |
| | A more prominent than usual population of micro follicles may occur (and may be disproportionately apparent on a minority of smears) in a moderately or markedly cellular sample, but the overall proportion of micro follicles is not sufficient for a diagnosis of follicular neoplasm/suspicious for follicular neoplasm. |
| | A predominance of Hürthle cells in a sparsely cellular aspirate with scant colloid. Interpretation of follicular cell atypia is hindered by sample preparation artefact. Moderately or markedly cellular sample is composed of a virtually exclusive population of Hürthle cells, yet the clinical setting suggests a benign Hürthle cell nodule. |
| | There are focal features suggestive of papillary carcinoma, including nuclear grooves, enlarged nuclei with pale chromatin, and alterations in nuclear contour and shape in an otherwise predominantly benign-appearing sample. |
| | There are cyst-lining cells that may appear atypical owing to the presence of nuclear grooves, prominent nucleoli, elongated nuclei and cytoplasm, and/or intranuclear cytoplasmic inclusions in an otherwise predominantly benign appearing sample. |
| | A minor population of follicular cells show nuclear enlargement, often accompanied by prominent nucleoli. |
| | There is an atypical lymphoid infiltrate (in which a repeated aspirate for flow cytometry is desirable), but the degree of atypia is insufficient for the general category "suspicious for malignancy". |
| Follicular neoplasm/ suspicious for follicular neoplasm | Sample contains cells with cytomorphologic features that distinguish them from benign follicular nodules. |
| | Disturbed cytoarchitecture: follicular cells are arranged predominantly in micro follicular or trabecular arrangements. |
| | Cellular crowding and overlapping with larger than normal follicular cells. Majority of the follicular cells are arranged in abnormal architectural groupings. |
| Suspicious for malignancy | Sample contains a few malignant-appearing cells which are poorly preserved, or too few cells for confident diagnosis, or is obscured by inflammation, blood, or cell debris |
| | The sample is adequate and there are some features of malignancy, but it lacks overtly malignant cells |
| | The clinical history suggests caution despite a few malignant-appearing cells present (e.g., cavitating TB or bronchiectasis, viral cytopathic effect, and chemotherapy or radiotherapy effect) |
| | The smear background suggests tumour necrosis, although well-preserved malignant cells are not identified |
| | The cytologic criteria of malignancy overlap with benign lesions |

All of the categories described in Table 1 can be described as atypical and indeterminate for cancer and therefore are not informative for reaching a cancer diagnosis. In the context of the present disclosure, these categories are an "inconclusive cytological assessment of cell morphology".

Resolving an Inconclusive Cytological Assessment of Cell Morphology

As used herein, the term "resolving" refers to the resolution of an inconclusive cytological assessment to determine the clinical status of a sample. Previously, it has been difficult to resolve an inconclusive cytological assessment of cell morphology to identify malignant cells and determine whether a subject has cancer. For example, it is typically reported by leading uropathology laboratories that 20-25% of all urine cytologies are inconclusive. However, this figure may vary between 10 and 40% (Raab et al., 2007; Zaak et al., 2001; Schneeweiss et al., 1999). The use and accuracy of cytology is fundamental in conventional practice to diagnosis and subsequent management of bladder cancer patients. Accordingly, resolving "inconclusive" cytologyical assessments to determine clinical status would be extremely valuable in up to 40% of all cases.

It has now been found that an inconclusive cytological assessment on the basis of morphology can be resolved to determine clinical status using a telomerase immunostaining test and further cytological assessment to detect binding of an anti-telomerase antibody to clinically relevant cells.

An advantage of this approach is that binding of an anti-telomerase antibody can be detected in individual clinically relevant cells. For example, binding of an anti-telomerase antibody can be detected in individual bladder urothelial cells obtained from a urine sample.

In particular, the present inventors have found that the binding of an anti-telomerase antibody to one or more clinically relevant cells in a sample from a subject indicates that the subject has cancer. As would be appreciated by one of skill in the art, an indication of cancer also indicates the presence of malignant cells in the sample. In performing the present method, telomerase can be present in more than one clinically relevant cell and indicate that a subject has cancer. In various embodiments, binding of an anti-telomerase antibody to at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 30, at least about 40, at least about 50, at least about 60, at least about 70, at least about 80, at least about 90, at least about 100, at least about 200 clinically relevant cells cytologically assessed in a sample from a subject indicates that the subject has cancer. In contrast, the absence of anti-telomerase antibody binding to clinically relevant cells indicates that malignant cells are not present in the sample.

More particularly, the present inventors have found that the binding of an anti-telomerase antibody to one or more clinically relevant cells in a sample with "atypical" cytology from a subject indicates that the subject has cancer. In various embodiments, binding of an anti-telomerase antibody to at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 30, at least about 40, at least about 50, at least about 60, at least about 70, at least about 80, at least about 90, at least about 100, at least about 200 clinically relevant cells with "atypical" cytology in a sample from a subject indicates that the subject has cancer. In contrast, the absence of anti-telomerase antibody binding to clinically relevant cells with "atypical" cytology indicates that malignant cells are not present in the sample.

Further, telomerase can be present in a percentage of the total number of clinically relevant cells cytologically assessed and indicate that a subject has cancer. In various embodiments, binding of an anti-telomerase antibody to at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 30%, at least about 40%, at least about 50%, at least about 60%, at least about 70%, at least about 80%, at least about 90% of clinically relevant cells cytologically assessed in a sample from a subject indicates that the subject has cancer.

In one example, binding of an anti-telomerase antibody to at least about 5% of clinically relevant cells cytologically assessed in a sample from a subject indicates that the subject has cancer. For the avoidance of doubt, it is envisaged that binding of an anti-telomerase antibody to one cell per 20 clinically relevant cells indicates that the subject has cancer.

In various embodiments, binding of an anti-telomerase antibody to at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 30%, at least about 40%, at least about 50%, at least about 60%, at least about 70%, at least about 80%, at least about 90% of clinically relevant cells with "atypical" cytology in a sample from a subject indicates that the subject has cancer.

Again, for the avoidance of doubt, it is envisaged that binding of an anti-telomerase antibody to one cell with "atypical" cytology per 20 clinically relevant cells indicates that the subject has cancer.

In one example, binding of an anti-telomerase antibody to at least about 5% of clinically relevant cells with atypical cytology cytologically assessed in a sample from a subject indicates that the subject has cancer.

In contrast, the absence of anti-telomerase antibody binding to clinically relevant cells indicates that the cells in the sample are not malignant.

In some embodiments, the sensitivity and/or specificity are measured against a clinical diagnosis of cancer.

In various embodiments, the sensitivity achieved by the presently claimed method for prognosing or determining whether a subject has cancer is at least about 50%, at least about 60%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%.

In various embodiments, the specificity achieved by the presently claimed method for prognosing or determining whether a subject has cancer is at least about 50%, at least about 60%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, or at least about 95%.

Detecting Anti-Telomerase Antibody Binding

Telomerase is a naturally occurring enzyme that maintains the length of telomeres at the end of a chromosome. In humans, telomerase is over-expressed in human stem cells, in germ line cells and in malignant cells. The function of telomerase is to synthesise new single stranded TTAGGG repeats at the end of each chromosome. In normal cells, telomerase plays a protective role by permitting a cell to multiply, thus preventing shortening of telomeres and avoiding cellular senescence (Bodnar et al., 1998). In contrast, albeit with the same mode of action, telomerase can also exhibit cancer-promoting properties in cells which are or may become malignant. In the absence of senescence, cells (tumours) replicate indefinitely, thereby introducing and propagating mutations (Blackburn et al., 2005). This cancer-promoting property of telomerase aids the immortality of the cell and development of cancer. Its association to cancer is evident in that its presence is observed as a common feature in nearly all tumour cells.

The present disclosure seeks to resolve an inconclusive cytological assessment of cell morphology by detecting whether telomerase is present in a sample. To detect telomerase, a cell sample from a subject is contacted with an antibody that binds telomerase, also referred to as an anti-telomerase antibody. It is considered that terms such as 'contacting', 'exposing' or 'applying' are terms that can, in context, be used interchangeably in the present disclosure. The term contacting, requires that the anti-telomerase antibody be brought into contact with a cell sample to detect whether telomerase is present in one or more cells in the sample. The binding of an antibody to telomerase indicates that telomerase is present in the cell. Further, the presence of telomerase in a sample may also be referred to as telomerase positive or positive for telomerase. The binding of an antibody to telomerase is detected via cytological assessment. For example, a light microscope may be used to detect binding of an antibody to telomerase in a clinically relevant cell.

Detecting the binding of an anti-telomerase antibody to clinically relevant cells in methods of the disclosure may be accomplished by any antibody/antigen binding detection technique known in the art where binding of the antibody to the antigen in clinically relevant cells can be detected via cytological assessment. For example, an immunoassay incorporating an anti-telomerase antibody may be used. In this example, cytology is used to detect binding of the anti-telomerase antibody to telomerase. In methods of the disclosure, telomerase is the "antigen". It is also envisaged that telomerase detection methods may be incorporated into an automated telomerase detection system. Such an automated immunoassay system would provide for the automatic processing of a sample and cytological detection of telomerase. It is envisaged that such a system would allow high throughput analysis of telomerase in samples.

Immunoassay

For routine clinical assessment it is envisaged that methods based on an immunoassay format will be used to detect the presence of telomerase in a sample. In the context of the present disclosure, an immunoassay is a biochemical test that measures the presence or concentration of an antigen in a solution through the use of an antibody or immunoglobulin.

The antibody used in the present disclosure can be any antibody that can detect whether telomerase is present in one or more cells in the sample. Various commercially available antibodies that can detect whether telomerase is present in a cell are available for use in the methods of the disclosure. Such antibodies can be obtained from Sapphire Biosciences, Life Span Biosciences, Novus Biologicals, Australian Biosearch, Epitomics, Santa Cruz, EMD Millipore, GenWay Biotech Inc, Jomar Biosciences, Sigma-Aldrich, BioCore Pty Ltd, US Biologicals, Thermo Scientific, Life Research, Resolving Images, Leica microsystems and Sienna Cancer Diagnostics Ltd. In an example, the antibody binds the telomerase complex (including each of human telomerase reverse transcriptase, telomerase RNA (TR or TERC), and dyskerin (DKC1) and/or Telomerase reverse transcriptase (hTERT). Preferably, the antibody is an anti-hTERT antibody. Most preferably, the antibody that binds telomerase is SCD-A7, 2D8, C-12, H-231, anti-telomerase catalytic subunit, 10E9-2, 2C4, and tel 3 36-10.

These antibodies are known in the art. For example, the anti-hTERT (tel 3) antibody is a monoclonal antibody produced from the hybridoma clone, 36-10. To purify the antibody, the IgG fraction of ascites was purified by Protein G affinity chromatography. The anti-hTERT (Clone SCD-A7) antibody is an IgM mAb, produced from the hybridoma clone, HJ123-2C4 (Masutomi et al., 2003) grown in hollow fibre cultures. In producing this antibody, amino-terminal FLAG epitope-tagged hTERT purified from baculovirus vector-infected insect cells was used as an immunogen to stimulate the production of anti-hTERT Clone SCD-A7 mAb.

The anti-hTERT (Clone 2C4) antibody is described in (Masutomi et al., 2003). In producing this antibody, amino-terminal FLAG epitope-tagged hTERT purified from baculovirus vector-infected insect cells was used as an immunogen to stimulate the production of anti-hTERT Clone 2C4 mAb. 2C4 is an IgM mAb, produced from the hybridoma clone, HJ123-2C4 grown in hollow fibre cultures.

Antibodies used in the methods of the present disclosure are also commercially available such as 2D8 (Novus NB100-297), C-12 (Santa Cruz 377511), H-231 (Santa Cruz 7212), anti-telomerase catalytic subunit (Rockland 600-401-252), 10E9-2 (MBL M216-3), 2C4 (Novus NB100-317), SCD-A7 (Sienna Cancer Diagnostics P/N 01-5001).

In an example, the antibodies of the present disclosure are detectably labelled. Examples of detectable labels include the conjugation of a dye, fluorophore or other reporter molecule for assays, tracking or imaging.

The antibody used in the present disclosure is not limited to monovalent antibodies and multivalent antibodies represented by IgM but also includes bivalent antibodies represented by IgG, so long as they bind telomerase.

Further, the antibody used in the present disclosure is not limited to whole antibody molecules, but includes minibodies, diabodies and modified products thereof, so long as they bind telomerase.

A minibody comprises antibody fragments lacking a portion of a whole antibody (for example, whole IgG), and is not particularly limited so long as it has telomerase-binding ability. With the exception of telomerase binding ability, there are no particular limitations on the antibody fragments of the present disclosure, so long as they are portions of a whole antibody, but they preferably contain a heavy chain variable region (VH) and/or a light chain variable region (VL). Furthermore, as long as it has telomerase antigen-binding ability, part of VH and/or VL can be deleted. The variable region may be chimerized or humanized. Specific examples of the antibody fragments include Fab, Fab', F(ab')2, and Fv. Specific examples of minibodies include Fab, Fab', F(ab')2, Fv, scFv (single chain Fv), diabody, and sc(Fv)2 (single chain (Fv)2). Multimers of these antibodies (for example, dimers, trimers, tetramers, and polymers) are also included in the minibodies that can be used to detect telomerase.

A diabody is a dimer composed of two polypeptide chains, and generally, the polypeptide chains are individually linked by a linker of, for example, five residues or so, which is short enough to prevent binding between VL and VH in the same chain. VL and VH that are encoded by the same polypeptide chain have a short linker between them, and form a dimer because they cannot form a single chain variable region fragment. Therefore, diabodies have two antigen binding sites.

Preferably, the antibody that binds telomerase is monoclonal, polyclonal, bispecific, chimeric, recombinant, anti-idiotypic, humanized, single-chain antibody molecule, or antigen-binding fragments thereof.

In a preferred embodiment according to the present disclosure the method for detection of telomerase uses a telomerase-specific primary antibody. Binding of the primary antibody to telomerase can be visualised via various known methods. For example, a labelled secondary antibody that recognises the primary antibody could be used. In this example, the label could be an enzyme such as horse radish peroxidase, a radioactive isotope, a fluorescent reporter, an electrochemiluminescent tag. Binding of the labelled secondary antibody to the primary antibody would be detected via cytological assessment.

In a particular example, a sample is contacted with a telomerase-specific primary anti-hTERT antibody. The sample is then washed to remove any unbound primary antibody and then a secondary antibody specific for the primary antibody and linked to a peroxidase enzyme is applied to the sample. The sample is then washed to remove any unbound secondary antibody and 3,3'-Diaminobenzidine (DAB) is applied to the sample. The conversion of DAB into a coloured product is visualised by routine cytological assessment with the presence of a coloured product indicating that telomerase is present in the sample.

Cancer Types

In the claimed method, the cancer may be any cancer so long as the subject cancer cells express telomerase. Preferably the cancer is bladder cancer, pancreatic cancer, liver cancer, gall bladder cancer, thyroid cancer, breast cancer, lung cancer, mesothelioma, cervical cancer, ovarian cancer, kidney cancer, colorectal cancer, lymphoma. Most preferably, the cancer is bladder cancer.

As would be appreciated by one of skill in the art, each cancer type has various characteristics associated with cancer grade. These grades are generally dictated by the level of cancer spread or invasion into the surrounding tissues. For example, the later grades of cancer or "high grade" is generally associated with a higher potential for metastasis and a poorer prognosis. High grade cancers have generally spread from the tissue or organ of origin into the surrounding tissue or throughout the body. In contrast, "low grade" cancer can be characterized as carcinoma in situ (CIS) meaning that cells are abnormally proliferating but are still contained within the tissue or organ of origin.

In the context of bladder cancer, "High grade" or "higher grade" bladder cancer refers to a bladder cancer that is more likely to recur and/or progress and/or become invasive in a subject, including malignant cancers with higher potential for metastasis (bladder cancer that is considered to be more aggressive). Cancers that are not confined to the bladder (i.e. muscle-invasive bladder cancer) are considered to be more aggressive bladder cancers.

Low grades of bladder cancer can be characterized as carcinoma in situ (CIS) meaning that cells are abnormally proliferating but are still contained within the bladder. "Low grade" or "lower grade" bladder cancer refers to bladder cancer, including malignant cancers with lower potential for recurrence, progression, invasion and/or metastasis (i.e. bladder cancer that is considered to be less aggressive). Cancers that are confined to the bladder (i.e. non-muscle invasive bladder cancer, NMIBC) are considered to be less aggressive bladder cancer.

Low grade bladder cancer may be classified as benign. Benign bladder cancer constitutes a mass of cells that at the time of diagnosis lacks the ability to invade neighbouring tissue or metastasize. Benign bladder cancers generally have a slower growth rate than malignant cancers and the benign cells are usually well differentiated.

It is envisaged the present disclosure can be used to determine whether a subject has low grade cancer.

Sample Preparation and Analysis

In performing the methods of the disclosure a cell sample from a subject is required. As used herein, the term "sample" refers to a cell or population of cells or a quantity of tissue or fluid from a subject. Most often, the sample has been removed from a subject. The 'sample' includes extracts and/or derivatives and/or fractions of the sample. It is considered that terms such as 'sample' and 'specimen' are terms that can, in context, be used interchangeably in the present disclosure. In the present disclosure, any biological material can be used as the above-mentioned sample so long as it can be collected from the subject. It is contemplated that the sample used in the present disclosure be a biological sample from a human.

The sample may include material obtained from biopsy or resection. Preferably, the sample is a fluid sample. The fluid sample may include a variety of biological materials selected from but not limited to the group consisting of blood (including whole blood), blood plasma, blood serum, hemolysate, lymph, synovial fluid, spinal fluid, urine, bladder washings, bladder scrubbings, cerebrospinal fluid, semen, stool, sputum, mucus, amniotic fluid, lacrimal fluid, cyst fluid, sweat gland secretion, bile, milk, tears or saliva. In the context of bladder cancer, the fluid sample is a urine sample.

It is envisaged that samples used in the methods of the present disclosure can be obtained using techniques known in the art. For example, in the context of bladder cancer, biopsy and resection material can be obtained via cytoscopy. In the context of breast or thyroid cancer, the sample may be obtained via fine needle aspiration. Alternatively, bladder urothelial cells may be obtained from a urine sample supplied by a subject.

In one example, a sample used in the methods of the present disclosure is a patient sample comprising clinically relevant cells of inconclusive cytology. In this example, the clinically relevant cells of inconclusive cytology are identified before contacting the sample with an anti-telomerase antibody and detecting the presence or absence of binding of the antibody to the clinically relevant cells of inconclusive cytology.

It is envisaged that in performing the present method the cytological assessment of cell morphology and the cytological assessment for detection of telomerase may be performed on separate samples obtained from the same patient.

For example, a subject may provide two samples with one being sent for cytological assessment of cell morphology and the other for cytological assessment for detection of telomerase. In this example, a cytological assessment of cell morphology that is inconclusive for cancer can be resolved by cytological assessment for detection of telomerase, with the detection of telomerase in clinically relevant cells indicating that the subject has cancer.

However, in a clinical setting, obtaining an additional sample for further testing, e.g., from a patient whose cytological assessment of cell morphology revealed that one or more clinically relevant cells in the sample had an atypical cytological assessment for cell morphology, can be difficult and can delay further testing that is desirable. Further, when additional specimens need to be processed prior to testing, it is desirable to minimize the costs associated with processing (e.g., reagents, and the like).

Accordingly, it is preferable that the cytological assessment of cell morphology and the cytological assessment for detection of telomerase be performed on the same sample obtained from the subject.

It is envisaged that that the present method may be performed by preparing two separate slides with cells from the same sample. In this instance, one slide is sent for cytological assessment of cell morphology and the other for cytological assessment for detection of telomerase. The methods discussed below in Example 2 may be used to prepare slides.

The present inventors have found that when a cytological assessment of cell morphology is inconclusive for cancer, the binding of an anti-telomerase antibody to these cells indicates that the subject has cancer. Accordingly, it is preferable that the same slide be used for cytological assessment of cell morphology and the cytological assessment for detection of telomerase.

Clinically Relevant Cells

The phrase "clinically relevant cells" refers to those cells that the cytologist or cytopathologist is examining to determine the cancer status of the patient.

Clinically relevant cells will depend on the cancer being investigated and in the context of the present disclosure can include, ductal and lobular cells of the breast, respiratory cells of the lung, mucosal cells of the digestive tract, duct and islet cells of the pancreas, hepatocytes, follicular cells, mesothelial cells, germ cells, granulosa cells and epithelial cells of the ovary, glandular and basal cells of the prostate, epithelial cells of the ureter, urothelial cells, ductal and tubular cells of the kidney, endometrial cells.

The determination of cancer can be made because of the general principle that normal cells do not express telomerase while malignant cells express telomerase. However, as would be appreciated by one of skill in the art, there are exceptions to this general principle as certain non-malignant cell types also express telomerase. These cells are not considered clinically relevant and should be excluded from the assessment. Preferably, the excluded cells are selected from the group comprising, T-cells, B-cells, neutrophils, macrophages, granulocytes, dendritic cells, mast cells, memory-cells, plasma cells, eosinophils, seminal vesicle cells, sperm. Most preferably, the excluded cells are neutrophils, macrophages and eosinophils, seminal vesicle cells and sperm. These cells are not clinically relevant to the assessment of cancer and have a distinctly different morphology from clinically relevant cells and therefore can easily be excluded visually when performing the cytological assessment.

For example, when using the present methods to determine bladder cancer, there are several cell types which one of skill in the art would visually exclude from the cytological analysis. These cells include inflammatory cells such as neutrophils, macrophages and eosinophils, as well as renal tubular cells, seminal vesicle cells, sperm, and squamous cells. These cells are not clinically relevant to the assessment of bladder cancer and have a distinctly different morphology from clinically relevant normal urothelial cells (bladder wall cells) and therefore can easily be excluded visually when performing the cytological assessment.

Reflexive Testing

It is envisaged that the claimed method may be performed as a reflexive test. A "reflexive test" refers to a subsequent test (e.g., a second test) that is undertaken based upon the results obtained in a previous test (e.g., a first test). When determining whether a subject has cancer, cytological assessment of a sample can lead to a desire to test for another target. In the context of the present disclosure, the desire to test for another target (i.e. detect binding of an anti-telomerase antibody to clinically relevant cells) is driven by a cytological assessment of cell morphology that is inconclusive for the cancer which reveals one or more atypical cells in a sample.

Adjunctive Testing

It is also envisaged that the claimed method may be performed as an adjunctive test. A test that provides information that adds to or assists in the interpretation of the results of other tests, and provides information useful for resolving an inconclusive earlier assessment may be classified as an adjunctive test. In a clinical setting, a cytological assessment of cell morphology may be requested to determine whether a subject has cancer. However, the cytological assessment may be inconclusive for the cancer. Therefore, to assist in determining whether the subject has cancer, a further cytological assessment is performed to detect the binding of an anti-telomerase antibody to clinically relevant cells in a sample from the subject as an adjunct to the cytological assessment of cell morphology. In this context, the binding of an anti-telomerase antibody to one or more clinically relevant cells indicates that the subject has cancer, resolving the inconclusive cytological assessment of cell morphology.

In performing adjunctive testing it is envisaged that the cytological assessment of cell morphology can be performed at or about the same time as the cytological detection of telomerase. However, these steps may be performed separately.

Subjects

As used herein, the "subject" can be any organism which can have cancer. In a preferred embodiment, the subject is a mammal. The mammal may be a companion animal such as a dog or cat, or a livestock animal such as a horse or cow. In an embodiment, the subject is a human. Terms such as 'subject', 'patient' or 'individual' are terms that can, in context, be used interchangeably in the present disclosure.

If malignant cells are identified in a subject using the methods of the present disclosure the subject can be directed or prescribed treatment for cancer. For example, if bladder cancer is identified in a subject, the subject may be directed treatments such as surgical intervention such as cystectomy, chemotherapy, radiotherapy, immunotherapy, antibody therapy or combinations thereof.

It is envisaged that the method of the present disclosure can be used to determine whether any subject has cancer. Preferably, the method is used to determine cancer in a subject with symptoms that are indicative of cancer. For example, in the context of bladder cancer, the present method would be applicable to a subject presenting to the clinic with symptoms indicative of bladder disease such as haematuria (blood in the urine); urinary frequency urgency; burning sensation on urination.

A sample used in the present disclosure may also be obtained from a subject requiring regular surveillance to monitor for new or recurrent cancer. For example, cancer survivors may require regular surveillance to monitor for new or recurrent lesions. Clinicians presently rely on morphologic changes in samples recovered from these patients. Once an abnormal cytological assessment of cell morphology is identified in a sample, the patient undergoes further investigation to obtain another cytology sample and/or biopsy to identify and confirm the source of the first abnormal cell population. If cancer is identified, the patient is managed by a surgical procedure and/or intravesical chemotherapy or immunotherapy to eradicate the malignant cells. If a cytological assessment of cell morphology is inconclusive for cancer, a clinician can obtain a sample from the subject under surveillance and apply the present method to determine whether they have cancer. If cancer is determined, the patient can then undergo further investigation to confirm the source of the telomerase positive cell population.

In the context of bladder cancer, surveillance after treatment begins with urinary cytological assessment of cell morphology every 3 months for one to two years, depending on the patient's risk factors and cancer staging. Screening intervals for cytological assessment of cell morphology are extended, depending on previous cellular and cystoscopic findings. It is envisaged that cytological assessment to detect the binding of an anti-telomerase antibody to clinically relevant cells would be paired with the above referenced cytology surveillance regimen. If an inconclusive cytological assessment of cell morphology is resolved by detecting binding of an anti-telomerase antibody to clinically relevant cells, the patient can then undergo cytoscopy to confirm the source of the telomerase positive cell population.

Diagnostic Determination

It is envisaged that in performing the claimed method particular results for cytological assessment of telomerase and cytological assessment of cell morphology will be associated with a specific diagnostic determination for each subject. The telomerase and cell morphology results that may be obtained when performing the claimed method are summarised below in Table 2.

TABLE 2

Diagnostic determination and clinical outcome associated with cytological assessment of cell morphology and cytological assessment of telomerase results

| Cytological Assessment of Telomerase | Cytological Assessment of cell morphology | Diagnostic determination and Clincial Outcome |
|---|---|---|
| +ve | +ve | Positive telomerase and cytology results indicates the subject has cancer. Cystoscopic investigation or upper tract imaging is warranted. |
| +ve | −ve | Positive telomerase result indicates the subject has cancer. Cystoscopic investigation or upper tract imaging is warranted. |
| +ve | atypical | Positive telomerase result indicates the subject has cancer. Cystoscopic investigation or upper tract imaging is warranted |
| −ve | +ve | The high positive predictive value and specificity of cytology of cell morphology alone suggests subject has cancer. Cystoscopic investigation or upper tract imaging is warranted |
| −ve | −ve | Subject is disease free. |
| −ve | atypical | Subject potentially has benign/reactive changes which are not linked to cancer. |

The following results indicate that the subject has cancer and therefore cystoscopic investigation or upper tract imaging is warranted:
- The binding of an anti-telomerase antibody to clinically relevant cells and positive cytological assessment of cell morphology
- The binding of an anti-telomerase antibody to clinically relevant cells and negative cytological assessment of cell morphology
- The binding of an anti-telomerase antibody to clinically relevant cells and an inconclusive cytological assessment of cell morphology
- Although unlikely to occur given the matching sensitivities of both positive cytological assessment of cell morphology and the binding of an anti-telomerase antibody to clinically relevant cells; the absence of anti-telomerase antibody binding to clinically relevant cells and positive cytological assessment of cell morphology.

The absence of anti-telomerase antibody binding to clinically relevant cells and negative cytological assessment of cell morphology indicates that the cells in the sample are not malignant. Further, the absence of anti-telomerase antibody binding to clinically relevant cells and an inconclusive cytological assessment of cell morphology indicates that the subject potentially has benign/reactive changes which are not linked to cancer. Accordingly, further investigation via cystoscopy is not warranted.

In the context of the present disclosure, positive cytological assessment of cell morphology refers to the identification of cells having morphological changes indicative of cancer. Morphological changes that may be associated with cancer include enlarged nuclei with irregular size and shape, prominent nucleoli, scarce cytoplasm which may be intense or pale in colour. In contrast, negative cytological assessment of cell morphology is defined as the absence of any morphological changes indicative of atypia, or cancer.

Definitive Diagnosis

In applying the methods of the present disclosure to resolve an inconclusive cytological assessment for cancer and determine the clinical status of a sample whether a subject has cancer, it is considered that a diagnostic determination regarding the presence of a cancer can be made based on the binding of an anti-telomerase antibody to one or more clinically relevant cells from a cell sample obtained from a subject. However, the diagnostic determination may or may not be conclusive with respect to the definitive diagnosis upon which a treating physician will determine a course of treatment. Put another way, a diagnostic determination obtained using the techniques of the disclosure would be understood by one skilled in the art to refer to the process of attempting to determine or identify a possible cancer.

The methods of the present disclosure can be used in providing assistance in assessing the risk of cancer development and would be considered to assist in making an assessment of a pre-clinical determination regarding the presence, or nature, of a predisposition or precursor to cancer. This would be considered to refer to making a finding that a subject has a significantly enhanced probability of developing cancer.

It would be contemplated that the methods of the present disclosure could also be used in combination with other methods of clinical assessment of cancer known in the art in providing an evaluation of the presence of cancer or an increased risk of cancer.

The definitive diagnosis of the cancer status of a subject determined to have cancer can be validated or confirmed if warranted, such as through imaging techniques including, PET, MRI, ultrasound, CT, PET/CT. Accordingly, the methods of the present disclosure can be used in a pre-screening or prognostic manner to assess whether a subject has cancer, and if warranted, a further definitive diagnosis can be conducted. In the context of the bladder cancer, investigation via cystoscopy with biopsy or upper tract imaging would be used to obtain a definitive diagnosis of the cancer status. It is also envisaged that the methods of the present disclosure may be useful for selecting patients for clinical assessment using previously validated diagnostic tests, in particular assessment via cystoscopy.

EXAMPLES

Example 1: Clinical Samples

An ethics-controlled and approved proof of concept study on clinical material from urological patients suspected of having, or with a history of, bladder cancer (urothelial cell carcinoma) was performed in order to demonstrate the clinical diagnostic potential of telomerase hTERT protein immunostaining. Furthermore, the study aimed to demonstrate that hTERT immunostaining can differentiate samples obtained from low grade versus high grade patients.

In this study, clinically positive patients had biopsy proven bladder cancer (including both non-invasive and muscle-invasive). All stage and grade determinations were by histology. In the case where a patient had multiple bladder cancer foci at different stages/grades, the higher stage/grade was recorded.

Clinically negative patients were all asymptomatic individuals in good health with no history of genitourinary disease or all disease-free patients presenting, for the first time or under monitoring for prior bladder cancer, for the visual inspection of the bladder wall (by flexible/rigid cystoscopy).

A patient was excluded from the study if any of the following criteria were met:
a) the patient had suspicious/uncharacterised non-bladder cancer diagnosis on visual inspection (flexible/rigid cystoscopy) with no histology performed;
b) monitoring patients that had a radical cystectomy;
c) patients with adenocarcinomas and non-urothelial bladder cancers (including small cell carcinoma, carcinosarcoma, primary lymphoma, and sarcoma; and/or
d) patients with other genitourinary tumours (kidney, prostate, upper ureter).

A total of 253 samples were originally tested. Of these, 108 samples were assessed using the protocol outlined below in Example 2 where a form of epitope retrieval was used either by freeze thaw or heat-induced. Of those, 90 samples had at least one urothelial (bladder wall) cell present. The remaining 18 samples were removed from all further analyses since no relevant bladder cell wall cells (i.e.: urothelial cells) were found. Of those 90 samples, five clinically positive samples were removed from further analysis due to the lack of biopsy-proven disease. The remaining 85 samples are represented in Table 3 (all clinically positive samples—biopsy-proven) and Table 4 (all clinically negative samples—cystoscopically clear), with cytological assessment of cell morphology and telomerase immunostain results shown for each. For the eighty-five samples analysed, the number of clinically relevant cells ranged from 5 to 3000 in both clinically positive and negative patients.

Clinically negative samples: Range 5-900 urothelial cells.
Clinically positive samples: Range 10-3000 urothelial cells.

For all patients, telomerase immunostaining and parallel-cytological assessment of cell morphology on the same sample was performed and the results recorded. Telomerase hTERT protein immunostaining and cytological assessment of cell morphology was performed blind of each other and blind of clinical status (obtained by cystoscopy+/−biopsy). Immunostaining, cytological assessment of cell morphology and cystoscopy were all performed by trained clinicians and/or pathologists, registered to perform these assays in their respective clinico-diagnostic and/or medical fields.

Scoring of the telomerase immunostaining was determined by a cytologist who scanned an adequate number of fields of view to obtain a confident assessment of the slide. The number/percentage of urothelial cells displaying nuclear staining was recorded by the reading cytologist. A cut-off value for test positivity was set at >5% of urothelial cells showing nuclear staining.

All samples (both clinically positive and negative) that were classified as atypical after cytological assessment of cell morphology are given in Table 5.

Example 2: Collection and Processing of Samples

Voided urine from patients was either processed immediately, or maintained at 4° C. for a period no longer than 4-6 hours prior to processing. Samples were transferred into sterile 50 mL centrifuge tubes and centrifuged at 600 g for 10 minutes at 4° C. The tubes were removed and the supernatant discarded. Cell pellets were resuspended in 15 mL 1×PBS and transferred into sterile 15 mL centrifuge tubes. Samples were re-centrifuged at 600 g for 10 minutes at 4° C. and the supernatant again discarded. Cell pellets were finally resuspended in 1 ml 1×PBS prior to cell counting.

Approximately 30,000 cells per sample were transferred to sterile 15 mL centrifuge tubes and the volume adjusted to 10 mL with Shandon Cytospin Collection Fluid (Thermo Scientific, Ref No: 6768001, Lot No: 226955). Tubes were again centrifuged at 600 g for 10 minutes at 4° C. The supernatant was discarded prior to resuspending in Shandon Cytospin Collection Fluid at a ratio of 250 µL per 30,000 cells. A Shandon Cytospin 4 (Thermo Scientific, Part No: A778300101, Serial No: CY6695 1055) was used to affix the cells to glass microscope slides by centrifuging the cells at 1000 rpm for 4 minutes with low acceleration.

Slides with affixed cells were stored in a microscope slide box at 4° C. overnight before transferring the slides into the −20° C. freezer.

All staining results reported herein were performed on Ventana Benchmark XT or Ventana Benchmark Ultra automated staining platforms. Identical results have been obtained, after optimisation, on other automated staining platforms including, but not limited to, Leica Bond and Biocare intelliPATH FLX. In addition to automated staining platforms, identical results have also been obtained, after optimisation, using a manual immuno staining process.

For the manual immunostaining process, slides were post-fixed in cold 50% acetone: methanol for 10 minutes. Slides were washed in 1× Phosphate buffered saline (PBS), pH 7.4, (Catalogue Number: 10010-023, 5×500 mL Gibco® by Life Technologies) to remove residual fixative and then placed in a staining dish containing citrate buffer pH 6.0. The slides are treated to a manual form of antigen retrieval for 30 minutes at 95° C. in a microwave oven. Slides are again washed in 1×PBS, pH 7.4. Post retrieval, slides were blocked with 5% BSA in 1×PBS with 0.5% Tween 20 for 1 hour, prior to incubating with the telomerase-specific primary anti-hTERT antibody at room temperature for 2 hours and washed in 1×PBS with 0.5% Tween 20. Slides are treated with a post-primary antibody block, Novacastra Post Primary (Ref: RE7159, Lot #6012593, 125 mL, Leica Microsystems) for 1 hour at room temperature and again washed in 1×PBS with 0.5% Tween 20. Slides are incubated with the secondary antibody Novacastra Novolink Polymer (Ref: RE7161, Lot #6012594, 125 mL, Leica Microsystems) for 30 minutes at room temperature and washed in 1×PBS with 0.5% Tween 20 prior to incubating with 3,3'-Diaminobenzidine (DAB) enhanced liquid substrate (Product Number: D3939, Sigma) for 2 minutes at room temperature. Slides are rinsed in 1×PBS, pH 7.4 to stop the reaction. Slides are then incubated in 0.5% Methyl Green solution at 60° C. for 5 minutes (Product Code: M8884-25G, Lot #MKBD8768V, 25 g, Sigma) and washed in tap water. Slides are dehydrated 0.05% (v/v) glacial acetic acid in acetone, then 95% ethanol, 100% ethanol followed by a final step in xylene. Slides are mounted with Ultramount No: 4 Mounting Media (Product Code: II065C, Batch #1305141450, 100 mL) and immediately a coverslip is applied before drying for 1 hour. Slides are observed under a light microscope.

For the automated immunostaining process, slides were post-fixed in cold 50% acetone: methanol for 10 minutes. Slides were washed/dipped in Ventana Antibody Dilution Buffer (Ventana Medical Systems, Inc Cat No: ADB250) to remove residual fixative and then placed on the automated staining platform and antigen retrieved on-board at 95° C. for 8 minutes. Post retrieval, slides were blocked with Ventana Discovery reagent (Ventana Medical Systems, Inc, Cat No: 760-108) for 4 minutes, prior to incubating with the telomerase-specific primary anti-hTERT antibody at 36° C. for 32 minutes. The remaining steps relied on standard Ventana platform settings using Ventana Discovery and Ventana UltraView Universal DAB Detection Kit (Ventana Medical Systems Inc, Cat No: 760-500). Hematoxylin counterstaining was performed off-board in a standard dip-dunk stainer. Counter staining could also be performed on-board to obtain identical results.

The results herein were obtained using the anti-hTERT (Clone 2C4) antibody described in (Masutomi et al., 2003).

TABLE 3

Cytological assessment of cell morphology and telomerase immunostain results in clinically positive samples (biopsy proven).

| # | ID | Cytological assessment of cell morphology* | Test result | % Urothelial cells stained |
|---|---|---|---|---|
| 1 | WH12-263 | Benign | Positive | 80 |
| 2 | AUA12-055 | Positive | Positive | 45 |
| 3 | WH12-278 | Positive | Positive | 12.5 |
| 4 | AUA12-057 | Atypical | Positive | 10 |
| 5 | AUA12-059 | Positive | Positive | 90 |
| 6 | WH12-287 | Positive | Positive | 75 |
| 7 | WH12-307 | Benign | Positive | 50 |
| 8 | WH12-320 | Positive | Positive | 40 |
| 9 | AUA12-087 | Positive | Positive | 100 |
| 10 | WH12-373 | Benign | Negative | 0 |
| 11 | WH12-390 | Benign | Negative | 0 |
| 12 | AUA12-088 | Positive | Positive | 80 |
| 13 | AUA12-090 | Benign | Negative | 1 |
| 14 | WH12-401 | Benign | Negative | 1 |
| 15 | WH12-406 | Atypical | Positive | 30 |
| 16 | WH12-407 | Benign | Negative | 0 |
| 17 | WH12-411 | Benign | Negative | 0 |
| 18 | RMH12-001 | Benign | Positive | 10 |
| 19 | WH12-422 | Positive | Positive | 95 |
| 20 | RMH12-010 | Atypical | Positive | 10 |
| 21 | WH12-424 | Benign | Positive | 10 |
| 22 | AUA12-101 | Positive | Positive | 80 |

*An "atypical" Cytological assessment of cell morphology indicates that cells in the sample have lost their normal appearance but have not reached the level of abnormality of malignant cells.
Sample re-stained

TABLE 4

Cytological assessment of cell morphology and telomerase immunostain results in clinically negative samples (biopsy proven).

| # | Sienna ID | Cytological assessment of cell morphology* | Test result | % Urothelial cells stained |
|---|---|---|---|---|
| 1 | AUA12-054 | Benign | Negative | 1 |
| 2 | WH12-268 | Benign | Positive | 10 |
| 3 | WH12-269 | Benign | Negative | 2 |
| 4 | WH12-274 | Benign | Negative | 0 |
| 5 | WH12-276 | Benign | Negative | 2 |
| 6 | WH12-279 | Benign | Negative | 0 |
| 7 | WH12-282 | Benign | Negative | 0 |
| 8 | AUA12-058 | Atypical | Positive | 20 |
| 9 | WH12-283 | Benign | Positive | 20 |
| 10 | WH12-284 | Benign | Negative | 1 |
| 11 | WH12-285 | Benign | Positive | 10 |
| 12 | WH12-286 | Benign | Negative | 0 |
| 13 | AUA12-060 | Benign | Negative | 1 |
| 14 | WH12-288 | Benign | Positive | 10 |
| 15 | WH12-290 | Benign | Negative | 0 |
| 16 | WH12-291 | Atypical | Positive | 15 |
| 17 | WH12-294 | Positive | Positive | 50 |
| 18 | WH12-295 | Benign | Negative | 0 |
| 19 | WH12-297 | Benign | Negative | 0 |
| 20 | WH12-298 | Benign | Negative | 0 |
| 21 | WH12-299 | Benign | Negative | 5 |
| 22 | WH12-301 | Benign | Negative | 1.5 |
| 23 | WH12-302 | Benign | Positive | 10 |
| 24 | WH12-304 | Benign | Negative | 1 |
| 25 | WH12-305 | Benign | Negative | 1 |
| 26 | WH12-309 | Benign | Negative | 2 |
| 27 | WH12-312 | Benign | Negative | 2 |
| 28 | WH12-313 | Benign | Positive | 20 |
| 29 | WH12-318 | Atypical | Positive | 10 |
| 30 | WH12-319 | Benign | Negative | 2 |
| 31 | WH12-322 | Benign | Negative | 1 |
| 32 | WH12-324 | Benign | Negative | 5 |
| 33 | WH12-326 | Benign | Negative | 0 |

TABLE 4-continued

Cytological assessment of cell morphology and telomerase immunostain results in clinically negative samples (biopsy proven).

| | | | Immunostaining result | |
|---|---|---|---|---|
| # | Sienna ID | Cytological assessment of cell morphology* | Test result | % Urothelial cells stained |
| 34 | WH12-327 | Benign | Negative | 0 |
| 35 | WH12-329 | Benign | Negative | 1 |
| 36 | WH12-330 | Benign | Negative | 1 |
| 37 | WH12-331 | Benign | Negative | 2 |
| 38 | WH12-332 | Benign | Negative | 1 |
| 39 | WH12-336 | Benign | Negative | 1 |
| 40 | WH12-337 | Benign | Negative | 1 |
| 41 | WH12-339 | Benign | Negative | 2 |
| 42 | WH12-341 | Benign | Negative | 2 |
| 43 | WH12-342 | Benign | Negative | 2 |
| 44 | AUA12-061 | Benign | Negative | 5 |
| 45 | AUA12-064 | Benign | Negative | 2 |
| 46 | AUA12-065 | Benign | Negative | 5 |
| 47 | AUA12-092 | Benign | Negative | 1 |
| 48 | WH12-368 | Benign | Negative | 2 |
| 49 | WH12-377 | Benign | Negative | 1 |
| 50 | WH12-378 | Benign | Positive | 10 |
| 51 | WH12-387 | Benign | Negative | 0 |
| 52 | WH12-396 | Benign | Negative | 0 |
| 53 | AUA12-093 | Benign | Negative | 5 |
| 54 | AUA12-095 | Benign | Negative | 1 |
| 55 | WH12-400 | Benign | Negative | 0 |
| 56 | WH12-410 | Benign | Negative | 0 |
| 57 | WH12-412 | Benign | Positive | 10 |
| 58 | RMH12-006 | Benign | Negative | 2 |
| 59 | RMH12-007 | Atypical | Negative | 5 |
| 60 | RMH12-008 | Benign | Positive | 20 |
| 61 | AUA12-098 | Benign | Positive | 20 |
| 62 | RMH12-009 | Benign | Positive | 10 |
| 63 | AUA12-099 | Benign | Negative | 0 |

*An "atypical" cytological assessment of cell morphology indicates that cells in the sample have lost their normal appearance but have not reached the level of abnormality of malignant cells.

Example 3: Immunostaining of Telomerase in Bladder Cancer Samples Correlates with Disease 85 clinical samples were processed onto microscope slides and stained using the protocol described above. Minor adjustments to antibody conditions or cell sample preparation were empirically determined on a sample-to-sample basis. Every sample that received telomerase immunostaining also underwent standard cytological assessment of cell morphology on the same sample. Cytological assessment of cell morphology was scored as positive, negative, or atypical.

Cytological assessment of cell morphology and telomerase immunostaining results were compared in clinically positive (Table 3) and clinically negative samples (Table 4). 22 clinically positive results were assessed with 16 having telomerase positive staining. Of the 6 remaining clinically positive samples 6 were identified as benign following cytological assessment of cell morphology. Accordingly, telomerase was indicative of 16 out of 22 (72%) malignant bladder cancers.

63 clinically negative samples were assessed with 48 (76%) having telomerase negative staining. Of the 15 remaining clinically negative samples, 11 (73%) were identified as benign following cytological assessment of cell morphology. The remaining 4 (27%) were identified as indeterminate (n=3) or positive (n=1) following cytological assessment of cell morphology.

Telomerase staining correlating with disease is shown in FIG. 1. No cellular staining was observed in sample WH11-107 (clinically negative; FIG. 1A). In contrast, significant cellular staining was observed in the clinically positive sample WH11-122 (FIG. 1B). In this sample, positive staining, in the form of strong nuclear staining was observed in 40-75% of the urothelial cells present, under optimal anti-

TABLE 5

Clinical status, cytological assessment of cell morphology and telomerase immunostain results in all samples (both clinically positive and negative) that had an atypical cytology.

| | | | | Immunostaining result | | |
|---|---|---|---|---|---|---|
| # | Sienna ID | Clinical status | Cytological assessment of cell morphology* | Test result | % Urothelial cells stained | Follow up clinical diagnosis |
| 1 | WH12-174^ | Positive | Atypical | Positive | 80 | |
| 2 | WH12-178 | Negative | Atypical | Negative | 0 | |
| 3 | WH12-197 | Negative | Atypical | Negative | 0 | |
| 4 | WH12-233 | Negative | Atypical | Negative | 0 | |
| 5 | WH12-234 | Negative | Atypical | Negative | 0 | |
| 6 | AUA12-057 | Positive | Atypical | Positive | 10 | |
| 7 | AUA12-058 | Negative | Atypical | Positive | 20 | Positive |
| 8 | WH12-289 | Positive | Atypical | Positive | 75 | |
| 9 | WH12-291 | Negative | Atypical | Positive | 15 | Positive |
| 10 | WH12-318 | Negative | Atypical | Positive | 10 | Cystectomy |
| 11 | WH12-353 | Negative | Atypical | Negative | 0 | |
| 12 | WH12-361 | Negative | Atypical | Negative | 0 | |
| 13 | WH12-374 | Negative | Atypical | Negative | 1 | |
| 14 | WH12-406 | Positive | Atypical | Positive | 30 | |
| 15 | RMH12-007 | Negative | Atypical | Negative | 5 | |
| 16 | RMH12-010 | Positive | Atypical | Positive | 10 | |

*An "atypical" cytological assessment of cell morphology indicates that cells in the sample have lost their normal appearance but have not reached the level of abnormality of malignant cells.
^Sample re-stained body concentrations. It was interesting to note that, not all the urothelial cells present in this clinical sample stained for the presence of telomerase hTERT protein, suggesting that not all cells within the sample were cancerous.

Example 4: Resolving False-Negative and Indeterminate Cytological Assessment of Cell Morphology Every sample (n=85) that received telomerase immunostaining also underwent standard cytological assessment of cell morphology on the same sample. Cytological assessment of cell morphology was scored as positive, negative, or atypical. All samples (both clinically positive and negative) that were classified as atypical following cytological assessment of cell morphology (n=16) are shown in Table 5 together with the associated scoring of the telomerase immunostaining.

The sixteen samples that had atypical cytology were evaluated using one of two different immunostaining protocols, with and without a form of epitope retrieval. There were eight samples in each protocol group, each giving similar results. Of the 16 samples, 5 samples were clinically positive and 11 were clinically negative. The telomerase immunostaining method assessed 5 of these 5 samples as positive (with >5% urothelial cells staining nuclear positive).

Of the 11 clinically negative samples, 8 were shown to be negative by the immunostain test, and three were shown to be positive. Of these three, two patients in longitudinal follow-up were later assessed to be clinically positive (biopsy-proven; clinical samples AUA12-058; WH12-291). The other sample is currently pending confirmatory clinical follow-up (WH12-318). However, this patient underwent cystectomy. Performance of this procedure indicates that the patient was positive for bladder cancer.

On the basis of current clinical status, the performance of the telomerase immunostain test is 80% in specificity and 83% in sensitivity, against cystoscopy. Furthermore, the immunostain result provided a correct diagnostic indicator (relative to cystoscopy) in at least 94% of cases (15 of 16), (likely 100% of cases; 16 of 16 as WH12-318 underwent cystectomy) where cytological assessment of cell morphology gave an inconclusive reading.

Example 5: Improving Diagnostic Readout

The unique method of preparing and immunostaining the clinical sample for the presence of telomerase, and simultaneously cytologically assessing the binding of an anti-telomerase antibody to clinically relevant cells and cytologically assessing cell morphology on a per-cell basis allowed for significant diagnostic improvements over cytological assessment of cell morphology alone.

In FIG. 3, the power of resolving an indeterminate cytological assessment of cell morphology result, or salvaging a false-negative cytological assessment of cell morphology result, through telomerase immunostaining on a per-cell basis, is shown. In this figure, the cells shown in all Panels are from a low grade bladder cancer clinical sample optimally immunostained for telomerase.

In Panel A, a non-bladder squamous cell is shown. This cell is not from the bladder and is visually excluded by trained cytologists from all diagnostic determinations. It serves as a negative immunostaining control in this clinical sample. As shown in panel A, the squamous cell is completely devoid of nuclear staining, as expected.

In Panel B, normal urothelial cells are shown. Both cells shown have well defined shapes and nuclear: cytoplasmic ratios. To a trained cytologist, these cells look completely normal, and would be appropriately defined as cytology negative following cytological assessment of cell morphology. The absence of nuclear immunostaining for telomerase hTERT protein suggests that these urothelial cells, although they were found in the voided urine of a patient known to have low grade bladder cancer, are very likely to be normal urothelial cells from a normal area of the bladder wall.

Panel C shows a morphologically normal urothelial cell of defined shape and nuclear: cytoplasmic ratio, yet in this case, strong nuclear immunostaining for telomerase hTERT protein is shown. This cytologically negative urothelial cell is, on the contrary, expressing abnormal levels of nuclear telomerase and is thus extremely likely to be an early stage malignant cell that has yet to show any morphological abnormalities. This conclusion is supported by the strong clinical correlation between telomerase hTERT immunostaining and clinical outcome shown in FIG. 2.

In the absence of telomerase immunostaining on the very same sample and the very same cell on which a determination was made based on a cytological assessment of cell morphology, this cell would have been defined as normal or non-cancer by a trained cytologist and/or pathologist. This would be incorrect and result in a false-negative call on that specific cell. Accordingly, the per-cell immunostaining of telomerase correctly determined this call.

In Panel D, a urothelial cell showing minor atypical traits, not strong enough to be called cytologically positive following cytological assessment of cell morphology by a trained cytologist, displays strong nuclear telomerase immunostaining. This is an example where individual cells classified as indeterminate after cytological assessment of cell morphology can still be resolved successfully by telomerase hTERT immunostaining under optimal conditions.

Example 6: Predicting Subsequent Development of Bladder Cancer

Three clinically negative samples, classified as inconclusive following cytological assessment of cell morphology were shown to be positive by the immunostain test. Of these three samples, two patients in longitudinal follow-up were later assessed to be clinically positive (biopsy-proven; clinical samples AUA12-058; WH12-291). The other sample is currently pending confirmatory clinical follow-up (WH12-318), however, this patient underwent cystectomy. Performance of this procedure indicates that the patient was positive for bladder cancer.

These data suggest that telomerase may be indicative of patients with increased risk of developing bladder cancer. Accordingly, patients clinically negative for cancer, which have provided samples that have positive telomerase staining, may be placed under increased clinical surveillance.

Example 7: Telomerase Staining in Clinical Setting to Diagnose Bladder Cancer

A patient presents to a clinic with symptoms indicative of bladder disease such as haematuria (blood in the urine), urinary frequency urgency or burning sensation on urination. While, these symptoms can be caused by other, much less serious conditions than cancer, such as a urine infection, they are characteristic of bladder cancer.

Accordingly, a urine sample is obtained from the patient and sent for cytological assessment of cell morphology and telomerase immunostaining. If the results of the cytological assessment of cell morphology are inconclusive for bladder cancer, the clinician can use the telomerase immunostaining results to determine whether the patient has bladder cancer.

If the sample is telomerase positive, the improved sensitivity of the telomerase assay over cytology at least warrants cystoscopic investigation for bladder cancer.

A cystoscopy can then be performed on the patient and if bladder cancer is subsequently identified, the appropriate treatment regimen can be established.

Example 8: Telomerase Staining in Clinical Setting to Identify Risk of Developing Bladder Cancer A urine sample is obtained from a patient presenting with similar symptoms to those discussed above. The sample is sent for cytological assessment of cell morphology and telomerase immunostaining. If the results of the cytological assessment of cell morphology are inconclusive and the sample is telomerase positive, the clinician can request cystoscopic investigation for bladder cancer.

If bladder cancer is not subsequently identified in the patient following cystoscopy, the evidence of the association between the binding of an anti-telomerase antibody to clinically relevant cells and cancer development indicates that the patient likely has an increased risk of cancer. Accordingly, the appropriate surveillance regimen can be established.

Example 9: Comparative Immunostaining of Telomerase in Bladder Cancer Samples Telomerase staining was compared in clinical samples using the methods outlined above in Example 2. Comparative immunostaining was performed using SCD-A7, Novus 2C4, Novus NB 100-297, Santa Cruz 377511, Santa Cruz 7212, Rockland 600-401-252 and MBL M216-3 antibodies. Comparative immunostaining results are shown in Table 6.

Accordingly, various anti-telomerase antibodies can be used to resolve inconclusive cytological assessments.

Example 10—Slide Reading Algorithm

Two slide reading algorithms have been evaluated utilising the clinical samples described in Example 1. The first algorithm involves counting of both urothelial and squamous cells with positive nuclear staining for telomerase. A positive test result is determined based on the percentage of cells stained. The second algorithm involves assessing morphological changes in urothelial cells in combination with positive nuclear staining for telomerase to derive a positive test result.

Reading Algorithm—5% Cut Off

Slides were assessed at a magnification of ×200-400 and visually scanned across an adequate number of fields of view to identify more than 20 urothelial cells. The following cell numbers were recorded:

1. The number of urothelial cells showing nuclear staining.
2. The number of urothelial cells identified/evaluated in the process of recording point (1) above.

The following particulars were also noted:

1. Urothelial staining characteristics (nuclear/cytoplasmic).
2. Percentage of squamous cells showing nuclear staining (including both cells with or without cytoplasmic staining).
3. Total number of squamous epithelial cells evaluated.

For this algorithm, a positive test result was defined as a slide in which more than 5% of the urothelial cells demonstrated positive nuclear staining (i.e. more than about 2 to 3 cells with positive nuclear staining per 20 urothelial cells).

Reading Algorithm—Morphology Based

Slides were assessed to identify urothelial cells demonstrating morphological atypia (e.g. high nuclear to cytoplasmic ratio, nuclear chromatin variation, irregular nuclear outlines). Cells demonstrating morphological atypia were then assessed for the presence or absence of a positive immunocytochemistry signal.

TABLE 6

Cytological assessment of cell morphology and telomerase immunostaining results in clinically validated samples (biopsy proven)

| Sienna ID | Clinical status | Cytological assessment of cell morphology* | Anti-telomerase antibody test result | | | | | | |
|---|---|---|---|---|---|---|---|---|---|
| | | | Sienna SC1-A7 | Novus 2C4 | Novus NB 100-297 | Santa Cruz SC-377511 | Santa Cruz SC-7212 | Rockland 600-401-252 | MBL M216-3 |
| AUA14-151 | Negative | Atypical | Negative | Negative | Negative | Negative | Negative | Negative | Negative |
| AUA14-160 | Positive | Atypical | Positive | # | # | # | # | # | Positive |
| AUA14-168 | Positive | Atypical | Positive | Positive | Positive | Positive | Positive | Positive | Positive |
| AUA14-173 | Positive | Atypical | Positive | # | # | Positive | Positive | # | # |
| AUA14-187 | Positive | Atypical | Positive | Positive | Positive | Positive | Positive | Positive | Negative |
| RMH13-058 | Positive | Atypical | Positive | # | Positive | # | # | # | # |
| RMH13-069 | Positive | Atypical | Positive | Positive | # | # | # | Positive | # |
| Correctly resolved inconclusive cytological assessment % | | | 7/7 | 4/4 | 4/4 | 4/4 | 4/4 | 4/4 | 3/4 |

%-2 samples excluded from analysis as clinical status could not be determined; AUA14-158; AUA14-172.
-Insufficient material available to stain.
*An "atypical" cytological assessment of cell morphology indicates that cells in the sample have lost their normal appearance but have not reached the level of abnormality of malignant cells.

Corresponding Papanicolau stained urine preparations were examined in conjunction with the telomerase immunocytochemistry slide during evaluation of clinical samples.

For this algorithm, a positive test result was defined as a slide in which the urothelial cells demonstrated morphological atypia in the presence of a positive nuclear stain.

Comparison of Reading Algorithms

Comparison of the above reading algorithms is summarised in Table 7. Review of slides using morphology in combination with telomerase positive staining of cells resulted in an overall sensitivity of 83.3% whereas the 5% Cut off Algorithm resulted in an overall sensitivity of 57.1%. The sensitivity for the detection of Low Grade urothelial carcinoma increased to 75.0% using the morphology based reading algorithm in comparison to 50.0% achieved with the 5% cut off algorithm.

The morphology based algorithm demonstrates increased sensitivity and specificity for the overall detection of urothelial carcinoma as well as increased sensitivity and specificity for both high and low grade disease classifications in comparison to the 5% cut off algorithm.

Nonetheless, the 5% cutoff algorithm also provided an effective approach for resolving an inconclusive cytological assessment in the analysed bladder cancer samples. For example, it is anticipated that 1 cell with positive nuclear staining per 20 urothelial cells indicates a positive test result.

TABLE 7

Comparison of the 5% Cut off and Morphology Based Algorithm results.

| Test Statistics | 5% Cut Off Algorithm | | | Morphology Based Algorithm | | |
| --- | --- | --- | --- | --- | --- | --- |
|  | Overall | High Grade Disease | Low Grade Disease | Overall | High Grade Disease | Low Grade Disease |
| Number | 31 | 20 | 27 | 27 | 18 | 23 |
| Sensitivity | 57.1% | 100.0% | 50.0% | 83.3% | 100.0% | 75.0% |
| Specificity | 58.8% | 58.8% | 58.8% | 86.7% | 86.7% | 86.7% |
| Likelihood Ratio for Positive Test (LR+) | 1.39 | 2.43 | 1.21 | 6.25 | 7.50 | 5.63 |
| Likelihood Ratio for Negative Test (LR−) | 0.73 | 0.00 | 0.85 | 0.19 | 0.00 | 0.29 |
| Positive Predictive Value (PPV) | 53.3% | 30.0% | 41.7% | 83.3% | 60.0% | 75.0% |
| Negative Predictive Value (NPV) | 62.5% | 100.0% | 66.7% | 86.7% | 100.0% | 86.7% |
| Diagnostic Accuracy | 58.1% | 65.0% | 55.6% | 85.2% | 88.9% | 82.6% |

It will be appreciated by persons skilled in the art that numerous variations and/or modifications may be made to the disclosure as shown in the specific embodiments without departing from the spirit or scope of the disclosure as broadly described. The present embodiments are, therefore, to be considered in all respects as illustrative and not restrictive.

The present application claims priority from AU 2014900494 filed 17 Feb. 2014, the disclosures of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

REFERENCES

Ausubel et al. (1988) Current Protocols in Molecular Biology, Greene Pub. Associates and Wiley-Interscience (including all updates until present).
Blackburn et al. (2005) Molecular Cancer Research 3, 477-482.
Bodnar et al. (1998) Science 279, 349-52.
Brown (1991) Essential Molecular Biology: A Practical Approach, Volumes 1 and 2, IRL Press.
Cibas et al. (2009) The Bethesda System for Reporting Thyroid Cytopathology, Am J Clin Pathol., 132, 658-665.
Coligan et al. (1994) Current Protocols in Immunology, John Wiley & Sons (including all updates until present).
Glover et al. (1991) DNA Cloning: A Practical Approach, Volumes 1-4, IRL Press.
Harlow and Lane (1988) Antibodies: A Laboratory Manual, Cold Spring Harbour Laboratory.
Parkin et al. (1999) CA Cancer J Clin 49, 33-64.
Perbal (1984) A Practical Guide to Molecular Cloning, John Wiley and Sons.
Masutomi et al., (2003) Cell, 114 (2), 241-253.
National Cancer Institute Fine-Needle Aspiration of Breast Workshop Subcommittees (1997) Diagn Cytopathol 16 (4), 295-311.
Raab et al. (2007) Am J Clin Pathol 127, 946-953.
Rosenthal et al. (2013) Cancer Cytopathol 121, 15-20.
Sambrook et al. (1989) Molecular Cloning: A Laboratory Manual, Cold Spring Harbour Laboratory Press.
Schneeweiss et al. (1999) J Urol 161, 1116-1119.
Suen et al. (1997) Diagn Cytopathol 17(4), 239-247.
Zaak et al. (2001) Urology 57, 690-694.

The invention claimed is:

1. A method for detecting bladder cancer epithelial cells comprising:
performing a cytological assessment of cells in a fluid sample comprising bladder epithelial cells, wherein said performing detects bladder epithelial cells having atypical cell morphology that is indeterminate of malignancy, wherein the sample is from a subject suspected of having bladder cancer;
contacting the sample with an anti-telomerase antibody; and
detecting binding of the anti-telomerase antibody to the bladder epithelial cells having atypical cell morphology that is indeterminate of malignancy.

2. The method of claim 1, wherein the performing cytological assessment and the detecting binding of the anti-telomerase antibody to the bladder epithelial cells are performed simultaneously on the same cells.

3. The method of claim 1, wherein the sample is selected from the group consisting of urine, bladder washings, bladder scrubbings.

4. The method of claim 1, wherein the sample is urine.

5. The method of claim 1, wherein said detecting binding of the anti-telomerase antibody is by an automated immunoassay.

6. The method of claim 1, wherein said detecting binding of the anti-telomerase antibody is by cytological assessment.

7. The method of claim 1, wherein the anti-telomerase antibody is monoclonal, bispecific, chimeric, recombinant, humanized, single-chain antibody molecule, or antigen-binding fragment of an anti-telomerase antibody.

8. The method of claim 1, wherein the anti-telomerase antibody is s polyclonal antibody.

\* \* \* \* \*